(12) United States Patent
Baschenis

(10) Patent No.: US 6,255,625 B1
(45) Date of Patent: Jul. 3, 2001

(54) AIR-OPERATED WAX GUN WITH REMOVABLY MOUNTED HEATER ON HOLLOW CENTRAL TUBE

(75) Inventor: Bruno Baschenis, Papeete (PF)

(73) Assignee: Creations des Mers du Sud Exploitation Sarl, Papeete (PF)

(*) Notice: Subject to any disclaimer, the term of this patent is extended or adjusted under 35 U.S.C. 154(b) by 0 days.

(21) Appl. No.: 09/510,080

(22) Filed: Feb. 22, 2000

(51) Int. Cl.$^7$ ........................................ B67D 5/62
(52) U.S. Cl. ........................ 219/227; 401/1; 222/146.5
(58) Field of Search ........................ 219/227, 424, 219/426, 420; 222/146.5, 191, 630, 568; 433/32; 401/1, 2, 3; 392/473, 474, 480

(56) References Cited

U.S. PATENT DOCUMENTS

| | | |
|---|---|---|
| D. 382,456 | 8/1997 | Granville, Jr. . |
| 1,333,458 * | 3/1920 | Sorver ........................ 401/2 |
| 1,767,079 * | 6/1930 | Kenyon ........................ 401/2 |
| 1,905,987 | 4/1933 | Lane . |
| 2,118,415 * | 5/1938 | Pesark ........................ 401/1 |
| 2,171,486 * | 8/1939 | Van Fleet ........................ 401/1 |
| 2,653,603 | 9/1953 | Hein, Jr. . |
| 3,364,577 * | 1/1968 | Oakleaf et al. ........................ 433/32 |
| 3,522,654 * | 8/1970 | Schoelz ........................ 401/2 |
| 3,554,408 | 1/1971 | Fremstad et al. . |
| 3,614,389 * | 10/1971 | Malisza ........................ 219/230 |
| 3,665,158 * | 5/1972 | Froedge ........................ 219/421 |
| 3,690,776 | 9/1972 | Zaporoshan . |
| 3,800,122 | 3/1974 | Farmer . |
| 3,831,815 | 8/1974 | Glasgow . |
| 3,902,043 | 8/1975 | Rogan . |
| 3,921,858 * | 11/1975 | Bemm ........................ 222/146.5 |
| 4,265,618 * | 5/1981 | Herskovitz et al. ........................ 433/32 |
| 4,301,357 | 11/1981 | Huffman . |
| 4,553,935 * | 11/1985 | Ueno ........................ 433/32 |
| 4,691,703 | 9/1987 | Auth et al. . |
| 4,813,870 | 3/1989 | Pitzen et al. . |
| 4,819,842 | 4/1989 | Westervelt . |
| 4,964,367 | 10/1990 | Belter . |
| 5,061,178 | 10/1991 | Ueno . |
| 5,346,394 | 9/1994 | Destafinis . |
| 5,524,809 | 6/1996 | Kosslow et al. . |
| 5,816,450 | 10/1998 | Alexander et al. . |

FOREIGN PATENT DOCUMENTS

| | | | |
|---|---|---|---|
| 3346254 * | 7/1985 | (DE) | ........................ 433/32 |
| 3611186 * | 10/1987 | (DE) | ........................ 433/32 |

* cited by examiner

Primary Examiner—John A. Jeffery
(74) Attorney, Agent, or Firm—James G. O'Neill

(57) ABSTRACT

The present invention provides an improved molten wax device for use in building patterns and forms in jewelry making and other applications. The device includes an insulating handle with a holding portion thereon which is held and manipulated between the thumb and fingers of a user's hand and includes a hollow central tube with an electrical heating element mounted thereon, and a removable dispensing tip at a first end thereof. A second end includes an elongated hollow inlet opening, to which an air hose may be connected so as to operate a slidable piston held within an internal bore to selectively extrude heated wax held within the internal bore through variable dispensing tips to form selected wax patterns.

22 Claims, 3 Drawing Sheets

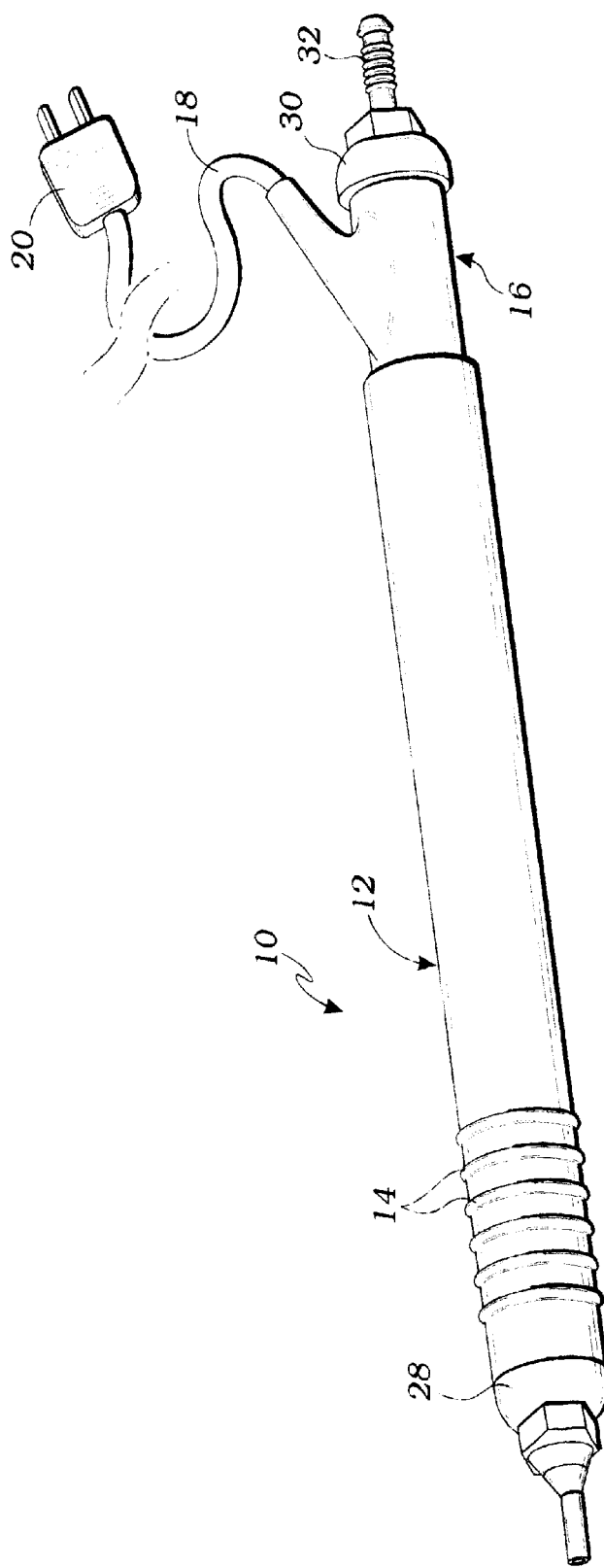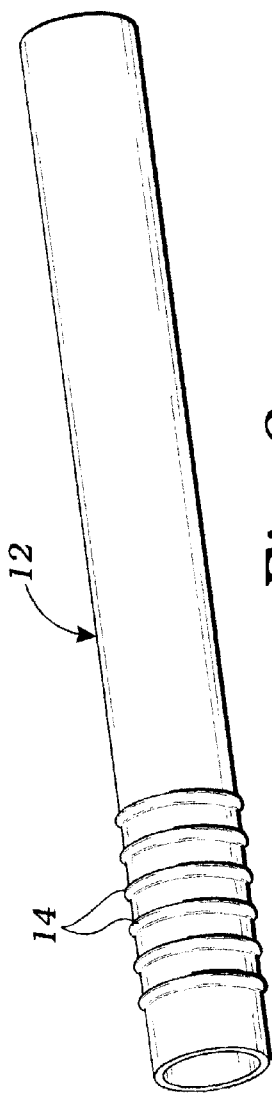
Fig. 1
Fig. 2

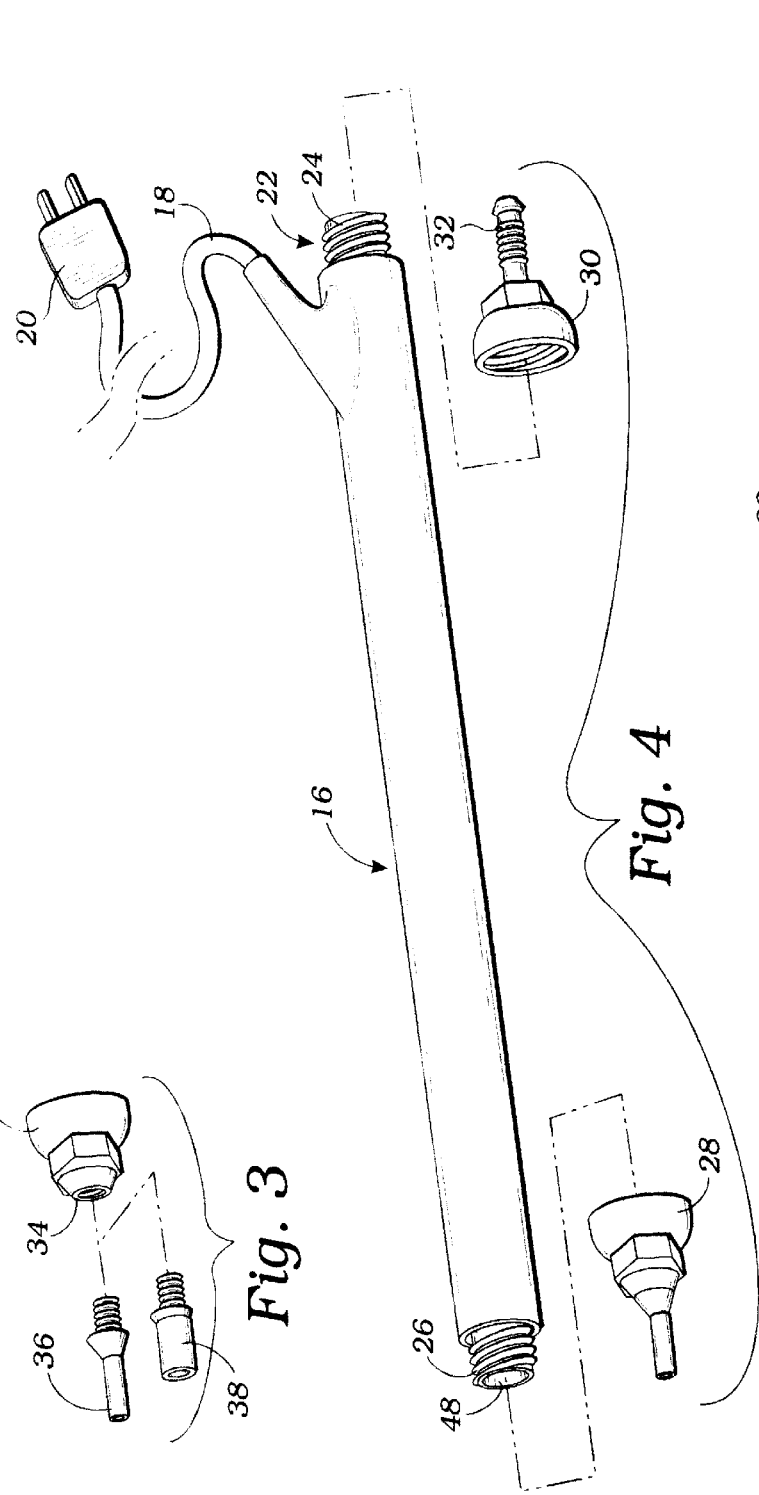
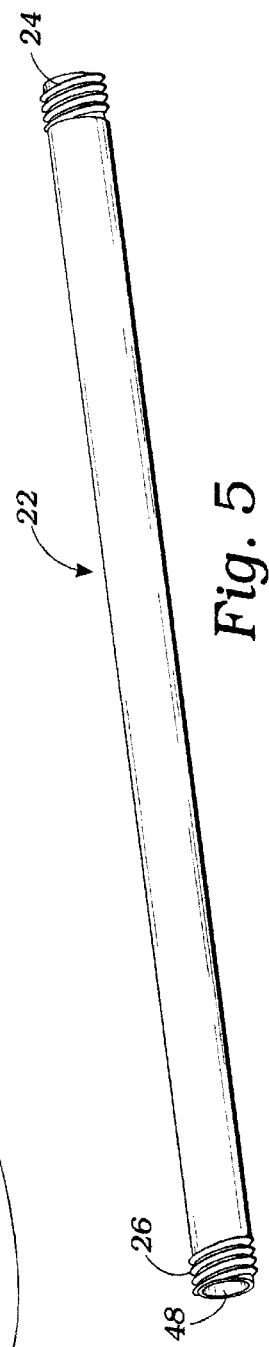
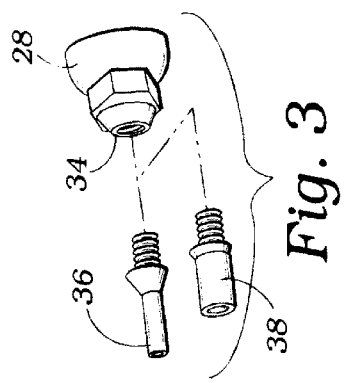

AIR-OPERATED WAX GUN WITH REMOVABLY MOUNTED HEATER ON HOLLOW CENTRAL TUBE

BACKGROUND OF THE INVENTION

1. Field of the Invention

This invention relates generally to electrically heated wax guns, and, more particularly, to an improved air-operated wax gun for making jewelry and the like.

2. Description of Related Art

Wax modeling for jewelry and sculpture is known. In particular, professionals who design jewelry have been using what has been referred to as a "MATT GUN" to transform sticks of hard wax into wire of different shapes and thickness. An important advantages of the Matt Gun lies in the fact that the extruded wire obtainable from a Matt Gun can vary in thickness so as to produce jewelry and miniature sculptures in three-dimensional character with a minimum of weight.

The Matt Gun has the ability to control pressure on the extruding wax, by means of a person's thumb pressing against a plunger, allowing a jewelry maker to produce constantly changing characteristics for their designs. Furthermore, because it is possible to vary the temperature of the Matt Gun, the extruded wax is more flexible and can be manipulated to a far greater extent than with conventional techniques or other known devices. Also, another advantage of the Matt Gun is that it uses a hard wax, therefore, eliminating the problems of damaged models made with any device that uses soft wax, or the like.

However, it has been found that the Matt Gun is not easy to use, and can cause fatigue in that it requires the user to press a plunger at the rear of the gun with their thumb, while attempting to hold the gun, and controlling the temperature of the gun, to extrude the wax out of the tip of the gun.

Other molten wax applicators and devices are known for use in the dental industry, or in the manufacture of various mechanical appliances. These devices tend to use softer waxes than the Matt Gun, and therefore, are not as useful in forming jewelry and small sculpture design. Examples of such known prior art devices are set forth in the following U.S. utility and design patents:

| | | | |
|---|---|---|---|
| 1,905,987 | 2,653,603 | 3,554,408 | 3,690,776 |
| 3,800,122 | 3,831,815 | 3,902,043 | 5,061,178 |
| 4,301,357 | 4,691,703 | 4,813,870 | 4,819,842 |
| 4,964,367 | 5,346,394 | 5,524,809 | 5,816,450 |
| | and Des. 382,456 | | |

Although the known prior art produce improved results, they still do not overcome the fatigue and other problems of handling when extruding hot wax from a gun encountered with the Matt Gun described above. Therefore, there exists a need in the art for an easily operated and less fatiguing device for extruding hard wax and forming jewelry and small sculpture designs.

SUMMARY OF THE INVENTION

It is, therefore, a general object of the present invention to provide an improved and simplified wax gun for designing jewelry. It is a particular object of the present invention to provide an improved air-operated wax gun for making jewelry and small sculpture designs. It is another particular object of the present invention to provide an improved air-operated wax gun having a piston operator held within an elongated tube, with a heating elements surrounding the elongated tube, and which is easily held and manipulated in a single hand of a user. And, it is still another particular object of the present invention to provide an improved air-operated wax gun which has a separate electrical heating element held between an insulating holder and an elongated cylindrical element having hard wax therein for extrusion out of changeable tips to form jewelry and small sculpture designs.

These and other objects and advantages of the present invention are achieved by providing a molten wax extruding device for building patterns and forms for jewelry and the like. The device has an elongated handle that is held and manipulated between the thumb and fingers of one hand, and also includes an elongated central tube with an electrical heating element held between the elongated central tube and the elongated handle. A dispensing tip is removably secured to a first end of the central tube, and an air-operated piston is held at a second end of the central tube with wax plugs inserted into the central tube, heated and extruded from the dispensing tip by movement of the piston.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, wherein like reference numerals are used throughout the several views, and, in which:

FIG. 1 is a perspective view of one embodiment of an air-operated wax gun of the present invention;

FIG. 2 is a perspective view of an insulating jacket or handle of the present invention removed from the wax gun;

FIG. 3 is an exploded view of a first end cap having an opening therein for selectively holding different size and shape tip elements;

FIG. 4 is an exploded perspective view of a heating element mounted on the elongated central tube with the ends caps removed;

FIG. 5 is a perspective view of the elongated central tube;

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide for an improved and simplified air-operated wax gun, generally indicated at 10.

Figure 8:
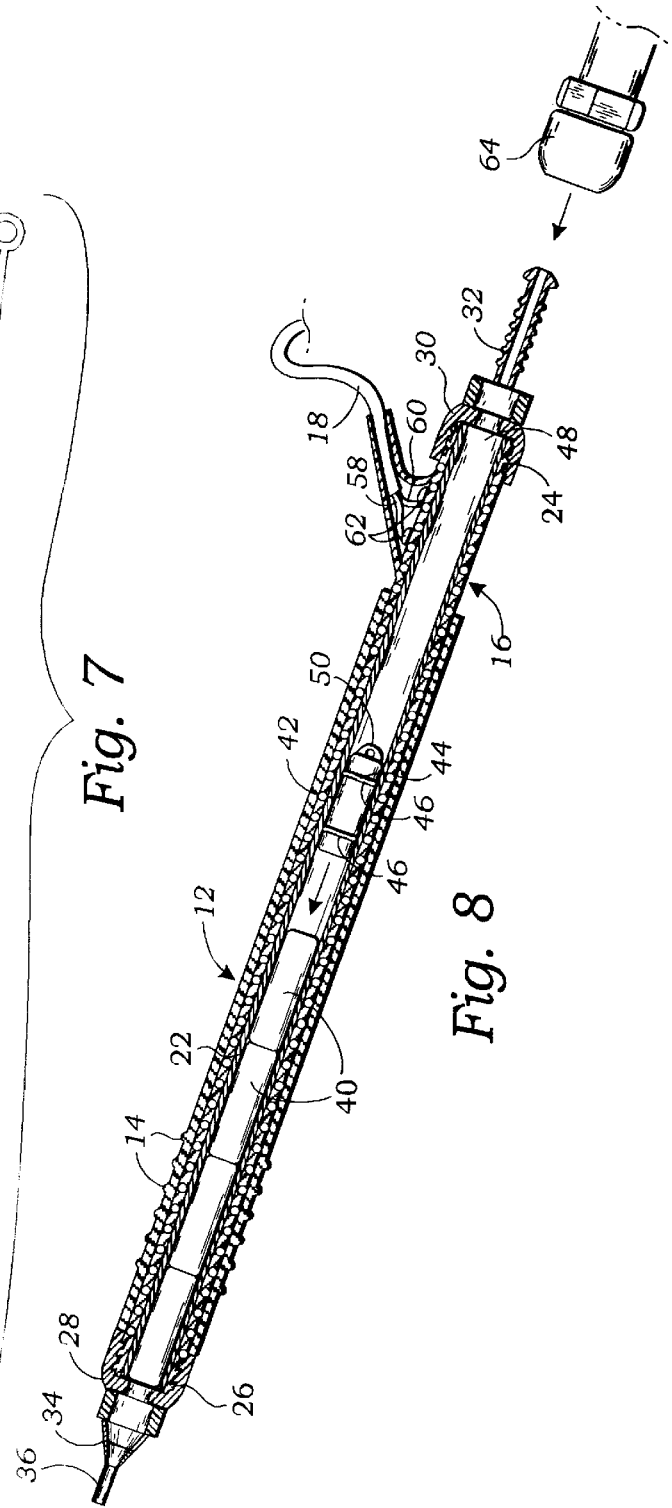
FIG. 8 is a cross-sectional perspective view of the device of FIG. 1, showing an end of an air hose, which may be connected to an elongated inlet opening at a second end of the device.

As shown in FIGS. 1 and 8, the air-operated wax device or gun 10 of the present invention includes an elongated tubular exterior insulating element or handle 12 made out of any desirable or known insulating material. The insulating handle or element 12 may include a plurality of raised portions or ridges 14 to enable a person to firmly grip the device between the fingers and thumb of one hand, for easy manipulation thereof.

The elongated tubular insulating element or handle 12 is slidably mounted over an elongated tubular heating element 16 having an electrical connector, such as a cord 18 and a plug 20, connected thereto. It is to be understood that a regulator or other variable control element may be connected to the cord 18 so as to vary the power applied to the electrical heating element 16 and thereby control the amount of heat applied by the heating element to melt wax. The heating element 16 is slidably mounted on an elongated central tubular element or housing 22, preferably made from a metal, such as aluminum, having threaded portions 24, 26 at opposite ends thereoL With the device of the present invention in the assembled condition, as shown in FIGS. 1 and 8, a first end cap 28 is mounted over the screw threads 26 at a first end of the tubular element 22, to hold the heating element and insulating handle in position. A further or second end cap 30 is secured to the screw threads 24 at the other or second end of tubular element 22. An elongated hollow inlet opening 32 is secured to the end cap 30 for connection to a hose 33, such as an air hose and a pneumatic system operator, such as a foot peddle operated valve, or the like (not shown). When the end caps 28, 30 are firmly secured on the threaded ends 26, 24 of the elongated, central tubular element 22, the heating element 16 and the insulating handle 12 will be immovably held thereon and the device will be ready for utilization, if wax plugs and a piston operator have been placed within the device.

As shown in FIG. 3, the first end cap 28, includes an internally threaded central opening 34 into which various size and shape dispensing tips, such as 36 and 38, may be inserted. Different size and shape openings in the dispensing tips 36 and 38 enable the device 10 to dispense various widths and shapes of wax. Each of the tips 36 and 38 as well as any other tips used, include threaded ends which are easily inserted in and removed from the internally threaded central opening 34 in the end cap 28.

When the cap 30 is removed from the threaded end 24 of the elongated central tubular elements 22, a plurality of hard wax plugs 40 (see FIGS. 6 and 8) may be inserted therein, after a piston 42, having a plurality of O-ring seals 44 held in grooves 46 formed in the piston is removed from an internal bore 48, extending along the entire length of the elongated tubular central element 22.

Figure 6:
FIG. 6 is an exploded perspective view of a plurality of wax elements for insertion into the elongated central tube, showing a piston operator and a pair of O-ring sealing elements.
Figure 7:
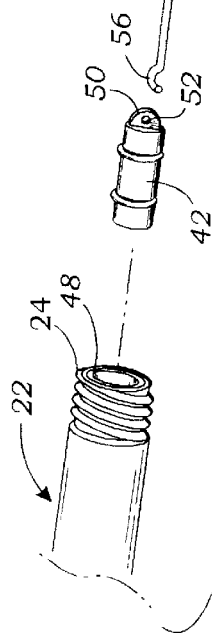
FIG. 7 is a partial exploded perspective view of an input end of the elongated central tube showing where the wax elements and the piston may be inserted in or pulled therefrom by a hooked element.

As shown in FIGS. 6–8, the piston element 42 includes an outer end 50 having an aperture or opening 52 formed therein. The aperture 52 enables an elongated pin 54 to be inserted within the bore 48, when the piston 42 is a away from the end 24 so that a hooked end 56 of the pin may be inserted into the aperture 52 and the piston 42 removed from the central bore 48. After removal of the piston 42, further wax elements or plugs 40 may be inserted in central bore 48, the piston 42 reinserted and the end cap 30 replaced, for use of the wax gun 10.

In use, the device 10 of the present invention is first loaded with a plurality of wax plugs 40, after unscrewing the end cap 30 from threaded end 24 and pulling the piston 42 out of bore 48 by means of the pin 54. After insertion of wax plugs 40 into the bore 48, the piston 42 is inserted back into bore 48, and end cap 30 screwed back onto threaded end 24. The air hose 33 is then secured over the elongated hollow inlet opening 32 and the cord 18 and/or the plug 20 inserted into a regulated power source. Power is then selectively applied to the heating element 16 to bring it to a desired temperature, whereby heat will be conducted through the elongated central element 22 to melt the wax plugs 40, a desired amount. A selected tip 36, 38, of any desired size or shape, is placed in the threaded opening 34, and air applied from hose 33 through the opening 32 so as to more piston 42 and extrude melted wax out the end of the dispensing tip held within the opening 34. The user may easily grip and move the device 10 to form any desired shape. The supply of air or other pneumatic fluid to the internal bore 48 through the opening 32 is controlled by a valve or other regulator means, such as a foot peddle. Therefore, a user easily manipulates the device of the present invention to form desired wax forms for jewelry or sculptures in an easy and simplified manner, without having to press on the end of a plunger, or the like. The present device enables the user to form designs in a less fatiguing and faster manner, using only one hand to grip the device.

It, therefore, can be seen that the device of the present invention provides an improved wax extrusion device to be used by a person in making jewelry and sculpture designs in a facile and improved manner, without the problems encountered with known devices.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. A wax gun for forming jewelry and sculpture designs, comprising, in combination:

an elongated tubular housing;

an elongated tubular heating element removably mounted on the elongated tubular housing;

an elongated tubular insulating element removably mounted on the elongated tubular heating element;

the elongated tubular housing having two end portions;

a piston slidably mounted in the elongated tubular housing; and end caps mounted on the two end portions.

2. The wax gun of claim 1 wherein the piston is sealingly mounted in an internal bore formed in the elongated tubular housing, between the end caps; and wherein the end caps are releasably mounted on the two end portions and secure the elongated tubular heating element and the elongated tubular insulating element on the elongated tubular housing.

3. A wax gun for forming jewelry and sculpture designs, comprising, in combination:

an elongated tubular housing;

an elongated tubular heating element removably mounted on the elongated tubular housing;

an elongated tubular insulating element removably mounted on the elongated tubular heating element;

the elongated tubular housing having threaded end portions and an internal bore extending between the threaded end portions;

a piston slidably and sealingly mounted in the internal bore; and end caps releasably mounted on the threaded end portions and holding the elongated tubular housing, the elongated tubular heating element and the elongated tubular insulating handle together to form the wax gun.

4. The wax gun of claim 3 wherein a first of the end caps has an opening formed therein and different size and shaped wax dispensing tips may be selectively inserted and held therein.

5. The wax gun of claim 4 wherein a second of the end caps includes an elongated inlet opening attached thereto, which elongated inlet opening is adapted to be connected to an air hose for operation of the piston in the internal bore.

6. The wax gun of claim 5, further including an electrical connector secured to the elongated tubular heating element for applying power thereto.

7. The wax gun of claim 6 wherein the piston includes a first or outer end having an aperture formed therein, whereby the piston may be removed from the internal bore by means of an elongated pin having a hook element formed at an inner end thereof, which inner end is insertable into the internal bore.

8. The wax gun of claim 7, further including a plurality of raised ridges on the elongated tubular insulating element.

9. The wax gun of claim 3 wherein one of the end caps is removed to enable the piston to be removed and hard wax plugs to be inserted in the internal bore.

10. The wax gun of claim 9 wherein the one of the end caps includes an elongated inlet opening attached thereto, which elongated inlet opening is adapted to be connected to an air hose for operation of the piston in the internal bore.

11. The wax gun of claim 10, further including an electrical connector secured to the elongate tubular heating element for applying power thereto.

12. The wax gun of claim 11 wherein the piston includes an aperture formed therein, which aperture may be captured by a hook to remove the piston from the internal bore.

13. The wax gun of claim 12 wherein a first of the end caps has a central opening formed therein and different size and shaped wax dispensing tips may by inserted and held therein.

14. The wax gun of claim 13, further including a plurality of raised ridges on the elongated tubular insulating element.

15. A wax gun to form molten wax into designs for jewelry and sculpture, comprising, in combination:
   an elongated, tubular, central metal housing having an internal bore extending along the entire length thereof;
   the elongated, tubular, central metal housing having a first threaded end and a second threaded end;
   a piston slidably held in the internal bore;
   an elongated, tubular, electrical heating element removably mounted on the elongated tubular, central metal housing;
   an elongated tubular insulating element removably mounted on the elongated tubular electrical heating element; and
   a first end cap releasably mounted on the first threaded end, and a second end cap releasably mounted on the second threaded end.

16. The wax gun of claim 15 wherein the first end cap has a threaded dispensing opening formed centrally therein, and a plurality of different molten wax dispensing tips may be selectively threaded into and removed from the threaded dispensing opening.

17. The wax gun of claim 16 wherein the second end cap includes an elongated inlet opening attached thereto, which elongated inlet opening is adapted to be connected to an air hose for operation of the piston in the internal bore.

18. The wax gun of claim 17 wherein the piston includes a first or outer end having an aperture formed therein, whereby the piston may be removed from the internal bore by means of an elongated pin having a hook element formed at an inner end thereof, which inner end is insertable into the internal bore.

19. The wax gun of claim 18, further including a plurality of raised ridges on the elongated tubular insulating element.

20. The wax gun of claim 15 wherein the second end cap is removed to enable the piston to be removed from the internal bore, and hard wax plugs to be inserted in the internal bore.

21. The wax gun of claim 19 wherein the piston includes an aperture formed therein, which aperture may be captured by a hook to remove the piston from the internal bore.

22. A wax gun to form molten wax into designs for jewelry and sculpture, comprising, in combination:
   an elongated, tubular, central metal housing having an internal bore therein;
   the elongated, tubular, central metal housing having a first threaded end and a second threaded end;
   a piston slidably held in the internal bore;
   a plurality of wax plugs held in the internal bore;
   an elongated tubular electrical heating element removably mounted on the elongated tubular, central metal housing;
   an elongated tubular insulating element removably mounted on the elongated tubular electrical heating element; the elongated tubular insulating element having a plurality of raised ridges thereon;
   a first end cap and a second end cap releasably mounted on the first threaded end and the second threaded end;
   the first end cap having a threaded, central dispensing opening formed therein, and a plurality of different molten wax dispensing tips for selectively threading into and removal from the threaded, central dispensing opening; and
   the second end cap includes an elongated hollow inlet opening attached thereto, which elongated hollow inlet opening is adapted to be connected to an air hose for operation of the piston in the internal bore.

* * * * *